US007601857B2

(12) United States Patent
Megati et al.

(10) Patent No.: US 7,601,857 B2
(45) Date of Patent: Oct. 13, 2009

(54) PREPARATION OF 6-HYDROXYEQUILENINS

(75) Inventors: Sreenivasulu Megati, New City, NY (US); Galina Vid, New City, NY (US); Arthur G. Mohan, Somerville, NJ (US); Panolil Raveendranath, Monroe, NY (US); John Potoski, West Nyack, NY (US)

(73) Assignee: Wyeth, Madison, NJ (US)

( * ) Notice: Subject to any disclaimer, the term of this patent is extended or adjusted under 35 U.S.C. 154(b) by 699 days.

(21) Appl. No.: 11/209,066

(22) Filed: Aug. 22, 2005

(65) Prior Publication Data

US 2005/0288268 A1 Dec. 29, 2005

Related U.S. Application Data

(62) Division of application No. 10/612,650, filed on Jul. 2, 2003, now Pat. No. 6,956,126.

(60) Provisional application No. 60/393,424, filed on Jul. 2, 2002.

(51) Int. Cl.
*C07J 1/00* (2006.01)
(52) U.S. Cl. ..................................... 552/615
(58) Field of Classification Search ........................ None
See application file for complete search history.

(56) References Cited

U.S. PATENT DOCUMENTS 6,956,126 B2 10/2005 Megati et al.
2003/0166627 A1 9/2003 Harris et al.

FOREIGN PATENT DOCUMENTS

WO WO 01/68669 A1 9/2001

OTHER PUBLICATIONS

Sakac et al, 1998, Journal of the Serbian Chemical Society, 63(1), pp. 21-24.*
International Search Report and Written Opinion, PCT/US06/032590, Jan. 24, 2007, 9 pages.
Koppl, A. et al., "Heterogeneous Metallocene Catalysts For Ethylene Polymerization", Journal of Molecular Catalysis, vol. 165, 2001, pp. 23-32.
Mendelsohn and Karas, "The protective effects of estrogen on the cardiovascular system," *New Engl. J. Med.*, 1999, vol. 340, 1801-1811.
Epperson, et al., "Gonadal steroids treatment of mood disorders," *Psychsomatic Med.*, 1999, vol. 61, 676-697.
Crandall, J. , "Estrogen replacement therapy and colon cancer: a clinical review," *Women's Health Gender-Based Med.*, 1999, vol. 8: 1155-1166.
Monk and Brodaty, "Use of estrogens for the prevention and treatment of Alzheimer's disease," *Dementia & Geriatric Cognitive Disorders*, 2000, vol. 11, 1-10.
Hurn and Macrae, "Estrogen as a neuroprotectant in stroke," *J. Cerebral Blood Flow & Metab.*, 2000, vol. 20, 631-652.

Calvin, "Oestrogens and wound healing," *Maturitas*, 2000, vol. 34, 195-200.
Finking, et al., "The effects of estrogen in the cardiovascular system," *Zeitshrift fur Kardiologie*, 2000, vol. 89, 442-453.
Brincat, "Hormone replacement therapy and the skin," *Maturitas*, 2000, vol. 35, 107-117.
Al-Azzawi, "The menopause and its treatment in perspective," *Postgrad Med. J.* , 2001, vol. 77, 292-304.
Moggs and Orphanides, "Estrogen receptors: orchestrators of pleiotropic cellular response," *EMBO Reports*, 2001, vol. 2, 775-781.
Hall, et al., "The multifaceted mechanisms of estradiol and estrogen receptor signaling," *J. Biol. Chem.*, 2001, vol. 276, 36869-36872.
McDonnell, "The mechanism of action of steroid hormone receptors," in Principles of Molecular Regulation, (2000) pp. 351-361.
McKenna, et al., "Nuclear receptor coregulators: cellular and molecular biology," Endocrine Rev. (1999) 20:321-344.
Quaedackers, et al., "4-Hydroxytamoxifen trans-represses nucear factor kappa-B activity in human osteobastic U2-OS cells through estrogen receptor (ER)alpha and not through ERbeta," Endocrinol. (2001) 142:1156-1166.
Bhat, et al., "A novel estrogen receptor beta: identification and functional analysis of additional N-termainal amino acids," J. Steroid Biochem. Mol. Biol. (1998) 67:233-240.
Pelzer, et al., "Estrogen effects in the myocardium: inhibition of NF-kappaB DNA binding by estrogen receptor-alpha and -beta," Biochem. Biophys. Res. Comm. (2001) 286:1153-1157.
Levin, "Cell localization, physiology, and non-genomic actions of estrogen receptors," J. Appl. Physiol. (2001) 91:1860-1867.
Levin, "Cellular functions fo the plasma membrane estrogen receptor," Trends Endocrinol. Metab. (1999) 10:374-377.
Green, et al., "Human oestrogen reseptor cDNA: sequence, expression and homology to v-erb-A," Nature (1986) 320:134-139.
Kuiper, et al., "Cloning of a novel estrogen receptor expressed in rat prostate and ovary," Proc. Natl. Acad. Sci. USA (1996) 93:5925-5930.
Couse, et al., "Tissue distribution and quantitative analysis of estrogen receptor-alpha (ERalpha) and estrogen receptor-beta (ERbeta) messenger ribonucleic acid in the wild-type and ERalpha-knockout mouse," Endocrinol. (1997) 138:4613-4621.
Kuiper et al., "Comparison of the ligand binding specificity and transcript tissue distribution of estrogen receptors alpha and beta," Endocrinol. (1997) 138:863-870.
Sar and Welsch, "Differential expression of estrogen receptor-beta and estrogen receptor -alpha in the rat ovary," Endocrinol. (1999) 140:963-971.
Fitzpatrick, et al., "Expression of estrogen receptor-beta protein in rodent ovary," Endocrinol. (1999) 140:2581-2591.
Cowley, et al., "Estrogen receptors alpha and beta form heterodimers on DNA," J. Biol. Chem. (1997) 272:19858-19862.
McDonnell, J.,"Selective estrogen receptor modulators (SERMs): a first step in the development of perfect hormone replacement therapy regimen," Soc. Gynecolog. Invest. (2000) 7:S10-S15.

(Continued)

*Primary Examiner*—Zinna N Davis
(74) *Attorney, Agent, or Firm*—Pepper Hamilton LLP

(57) ABSTRACT

This invention relates to a process for the preparation of 6-hydroxyequilenins, which are useful as estrogenic agents.

5 Claims, No Drawings

OTHER PUBLICATIONS

Goldstein, "A pharmacological review of selective oestrogen receptor modulators," Human Reproduction Update (2000) 6:212-224.

Pike, et al., "Structure of the ligand-binding domain of oestrogen receptor beta presence of a partial agonist and a full antagonist," EMBO J. (1999) 18:4608-4618.

Shiau, et al., "The structural basis of estrogen receptor/coactivator recognition and the antagonism of this interaction by tamoxifen," Cell (1998) 95:927-937.

Ogawa, et al., "The complete primary structure of human estrogen receptor beta (hER-beta) and its heterodimerization with ER alpha in vivo and in vitro," Biochem. Biophys. Res. Comm. (1998) 243:122-126.

Paige, et al., "Estrogen receptor (ER) modulators each induce distinct conformational changes in ER alpha and ER beta," Proc. Natl. Acad. Sci. USA (1999) 96:3999-4004.

Schwarz, et al., *Tetrahedron*, 1994, vol. 50, 10709-10720.

Harnik, M., *Israel Journal of Chemistry*, 1965, vol. 3, 183-192.

* cited by examiner

PREPARATION OF 6-HYDROXYEQUILENINS

CROSS-REFERENCE TO RELATED APPLICATIONS

This application is a Divisional of U.S. patent application Ser. No. 10/612,650, filed on Jul. 2, 2003, now U.S. Pat No. 6,956,126 which claims priority benefit of U.S. Provisional Application Ser. No. 60/393,424 filed Jul. 2, 2002, each of which is hereby incorporated by reference in its entirety.

BACKGROUND OF THE INVENTION

This invention relates to a process for the preparation of 6-hydroxyequilenins, which are useful as estrogenic agents.

The pleiotropic effects of estrogens in mammalian tissues have been well documented, and it is now appreciated that estrogens affect many organ systems [Mendelsohn and Karas, New England Journal of Medicine 340: 1801-1811 (1999), Epperson, et al., Psychosomatic Medicine 61: 676-697 (1999), Crandall, Journal of Womens Health & Gender Based Medicine 8: 1155-1166 (1999), Monk and Brodaty, Dementia & Geriatric Cognitive Disorders 11: 1-10 (2000), Hum and Macrae, Journal of Cerebral Blood Flow & Metabolism 20: 631-652 (2000), Calvin, Maturitas 34: 195-210 (2000), Finking, et al., Zeitschrift fur Kardiologie 89: 442-453 (2000), Brincat, Maturitas 35: 107-117 (2000), Al-Azzawi, Postgraduate Medical Journal 77: 292-304 (2001)]. Estrogens can exert effects on tissues in several ways, and the most well characterized mechanism of action is their interaction with estrogen receptors leading to alterations in gene transcription. Estrogen receptors are ligand-activated transcription factors and belong to the nuclear hormone receptor superfamily. Other members of this family include the progesterone, androgen, glucocorticoid and mineralocorticoid receptors. Upon binding ligand, these receptors dimerize and can activate gene transcription either by directly binding to specific sequences on DNA (known as response elements) or by interacting with other transcription factors (such as AP1), which in turn bind directly to specific DNA sequences [Moggs and Orphanides, EMBO Reports 2: 775-781 (2001), Hall, et al., Journal of Biological Chemistry 276: 36869-36872 (2001), McDonnell, Principles Of Molecular Regulation. p351-361(2000)]. A class of "coregulatory" proteins can also interact with the ligand-bound receptor and further modulate its transcriptional activity [McKenna, et al., Endocrine Reviews 20: 321-344 (1999)]. It has also been shown that estrogen receptors can suppress NFκB-mediated transcription in both a ligand-dependent and independent manner [Quaedackers, et al., Endocrinology 142: 1156-1166 (2001), Bhat, et al., Journal of Steroid Biochemistry & Molecular Biology 67: 233-240 (1998), Pelzer, et al., Biochemical & Biophysical Research Communications 286: 1153-7 (2001)].

Estrogen receptors can also be activated by phosphorylation. This phosphorylation is mediated by growth factors such as EGF and causes changes in gene transcription in the absence of ligand [Moggs and Orphanides, EMBO Reports 2: 775-781 (2001), Hall, et al., Journal of Biological Chemistry 276: 36869-36872 (2001)].

A less well-characterized means by which estrogens can affect cells is through a so-called membrane receptor. The existence of such a receptor is controversial, but it has been well documented that estrogens can elicit very rapid non-genomic responses from cells. The molecular entity responsible for transducing these effects has not been definitively isolated, but there is evidence to suggest it is at least related to the nuclear forms of the estrogen receptors [Levin, Journal of Applied Physiology 91: 1860-1867 (2001), Levin, Trends in Endocrinology & Metabolism 10: 374-377 (1999)].

Two estrogen receptors have been discovered to date. The first estrogen receptor was cloned about 15 years ago and is now referred to as ERα [Green, et al., Nature 320: 134-9 (1986)]. The second form of the estrogen receptor was found comparatively recently and is called ERβ [Kuiper, et al., Proceedings of the National Academy of Sciences of the United States of America 93: 5925-5930 (1996)]. Early work on ERβ focused on defining its affinity for a variety of ligands and indeed, some differences with ERα were seen. The tissue distribution of ERβ has been well mapped in the rodent and it is not coincident with ERα. Tissues such as the mouse and rat uterus express predominantly ERα, whereas the mouse and rat lung express predominantly ERβ [Couse, et al., Endocrinology 138: 4613-4621 (1997), Kuiper, et al., Endocrinology 138: 863-870 (1997)]. Even within the same organ, the distribution of ERα and ERβ can be compartmentalized. For example, in the mouse ovary, ERβ is highly expressed in the granulosa cells and ERα is restricted to the thecal and stromal cells [Sar and Welsch, Endocrinology 140: 963-971 (1999), Fitzpatrick, et al., Endocrinology 140: 2581-2591 (1999)]. However, there are examples where the receptors are coexpressed and there is evidence from in vitro studies that ERα and ERβ can form heterodimers [Cowley, et al., Journal of Biological Chemistry 272: 19858-19862 (1997)].

A large number of compounds have been described that either mimic or block the activity of 17β-estradiol. Compounds having roughly the same biological effects as 17β-estradiol, the most potent endogenous estrogen, are referred to as "estrogen receptor agonists". Those which, when given in combination with 17β-estradiol, block its effects are called "estrogen receptor antagonists". In reality there is a continuum between estrogen receptor agonist and estrogen receptor antagonist activity and indeed some compounds behave as estrogen receptor agonists in some tissues and estrogen receptor antagonists in others. These compounds with mixed activity are called selective estrogen receptor modulators (SERMS) and are therapeutically useful agents (e.g. EVISTA) [McDonnell, Journal of the Society for Gynecologic Investigation 7: S10-S15 (2000), Goldstein, et al., Human Reproduction Update 6: 212-224 (2000)]. The precise reason why the same compound can have cell-specific effects has not been elucidated, but the differences in receptor conformation and/or in the milieu of coregulatory proteins have been suggested.

It has been known for some time that estrogen receptors adopt different conformations when binding ligands. However, the consequence and subtlety of these changes has been only recently revealed. The three dimensional structures of ERα and ERβ have been solved by co-crystallization with various ligands and clearly show the repositioning of helix 12 in the presence of an estrogen receptor antagonist which sterically hinders the protein sequences required for receptor-coregulatory protein interaction [Pike, et al., Embo 18: 4608-4618 (1999), Shiau, et al., Cell 95: 927-937 (1998)]. In addition, the technique of phage display has been used to identify peptides that interact with estrogen receptors in the presence of different ligands [Paige, et al., Proceedings of the National Academy of Sciences of the United States of America 96: 3999-4004 (1999)]. For example, a peptide was identified that distinguished between ERα bound to the full estrogen receptor agonists 17β-estradiol and diethylstilbesterol. A different peptide was shown to distinguish between clomiphene bound to ERα and ERβ. These data indicate that each ligand potentially places the receptor in a unique and unpredictable conformation that is likely to have distinct biological activities.

As mentioned above, estrogens affect a panoply of biological processes. In addition, where gender differences have been described (e.g. disease frequencies, responses to challenge, etc), it is possible that the explanation involves the difference in estrogen levels between males and females.

DESCRIPTION OF THE INVENTION

This invention provides a process for the preparation of compounds of formula I having the structure,

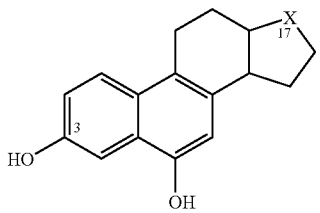

wherein,

-continued

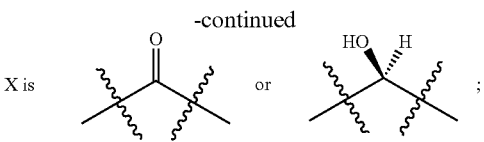

a pharmaceutically acceptable salt thereof, a pharmaceutically acceptable salt of a sulfate ester of the hydrdoxyl group at the 3- or 17-position, or a glucuronide of the hydrdoxyl group at the 3- or 17-position.

Pharmaceutically acceptable salts can be formed from organic and inorganic bases, such as alkali metal salts (for example, sodium, lithium, or potassium) alkaline earth metal salts, ammonium salts, alkylammonium salts containing 1-6 carbon atoms or dialkylammonium salts containing 1-6 carbon atoms in each alkyl group, and trialkylammonium salts containing 1-6 carbon atoms in each alkyl group. It is preferred that the pharmaceutically acceptable salt is sodium.

The reagents used in the preparation of the compounds of this invention can be either commercially obtained or can be prepared by standard procedures described in the literature.

The compounds of the present invention can be prepared according to the following synthetic scheme.

SCHEME I

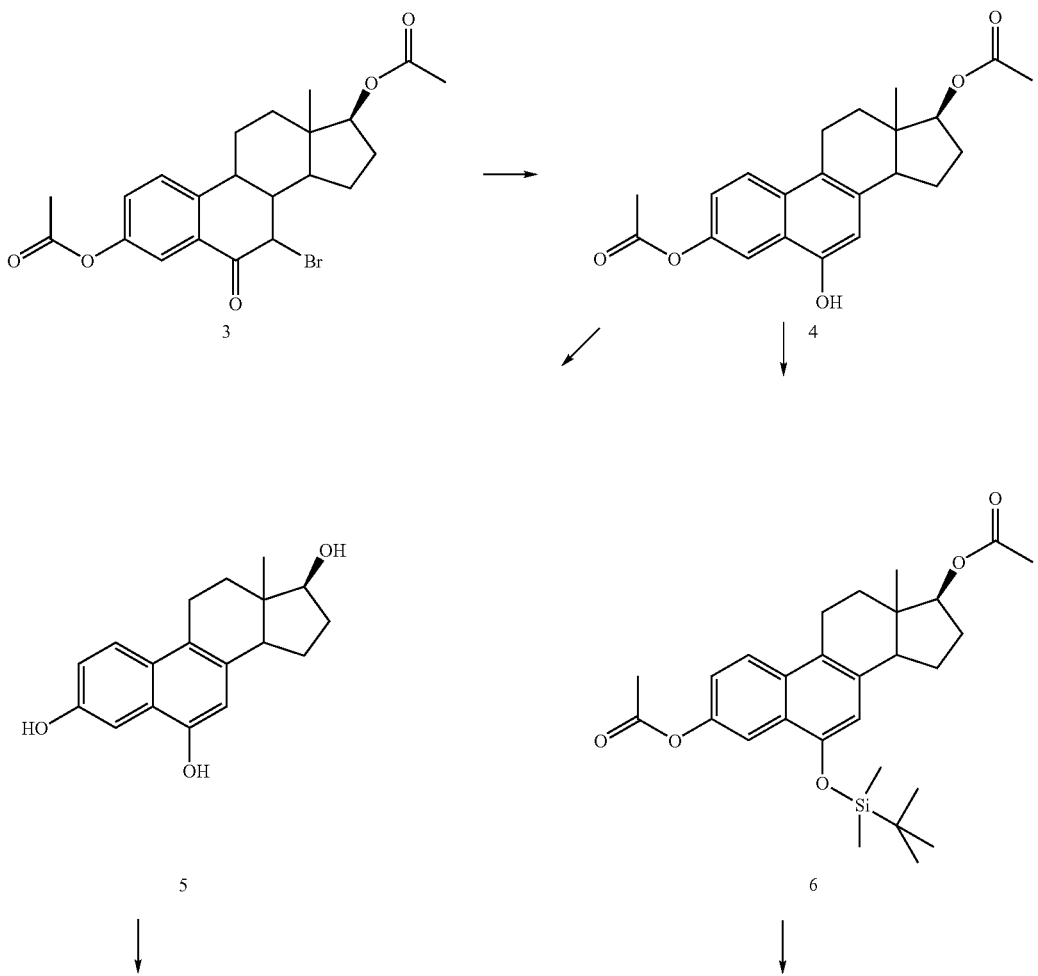

-continued

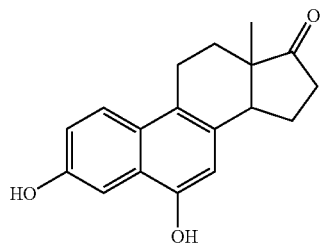

1

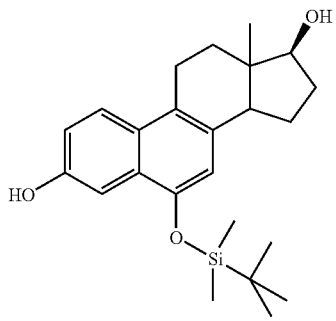

7

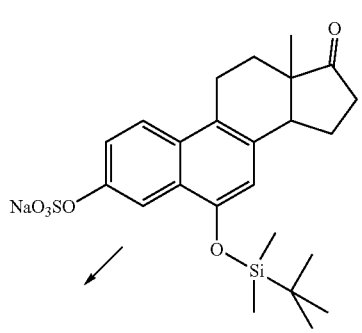

10

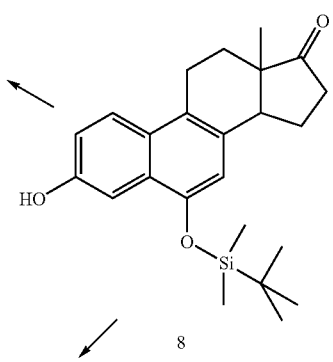

8

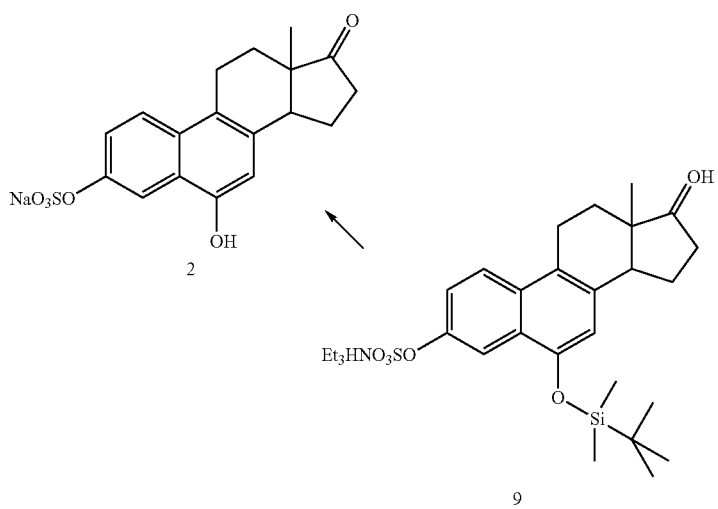

2

9

Referring to Scheme I, the common intermediate 6-hydroxyequilenin-3,17β-diacetate (4) can be prepared from 7-bromo-6-ketoestradiol-3-17β-diacetate (3) by elimination with alkali carbonates or bicarbonates, such as CaCO3 in a polar aprotic solvent, from ambient to 170° C., such as using refluxing dimethylacetamide [M. Harnik, Israel J. Chem, 1965, 3, 183-192].

Hydroysis of the acetyl protecting groups can be accomplished using inorganic bases in a protic solvent (0-40° C.) or under trans esterification conditions with alkali carbonates in alcoholic solvents to provide the 6-hydroxyequilenin-17β-ol (5). The 6-hydroxyequilenin (1) can be obtained by oxidation of compound 5 using chromium oxidizing agents; with DMSO/oxalyl chloride (Swern), sulfurtrioxide-triethylamine complex; (Shwarz., et al; Tetrahedron, 1994, 50, 10709-10720); or under Oppenauer oxidation conditions using Al(OC$_3$H$_7$)$_3$.

Sodium-6-hydroxyequilenin-3-sulfate (2) can be synthesized from the common intermediate, 6-hydroxyequilenin-3, 17β-diacetate (4) by protecting the 6-hydroxyl with a suitable silyl protecting group, such as a tert-butyldimethylsilyl group. Selective removal of the acetyl groups from 6-OTBDMS-equilenin-3,17β-diacetate (6) can be accomplished under trans esterification conditions with alkali carbonates, alkali bicarbonates, or alkali alkoxides in alcoholic or protic solvents affords the 6-OTBDMS-equilenin-3,17β-diol (7). The 17-hydroxy function can be oxidized under a variety of conditions (such as using chromium based agents, Swern conditions, Oppenauer conditions, and the like) to 17-keto to give 6-OTBDMS-equilenin (8). The latter (8) can be sulfated at the 3-hydroxy position with sulfurtrioxide-triethylamine complex followed by treatment with aqueous sodium carbonate affords (10). Intermediate (9) triethylammonium-6-OTB-DMS-equilenin-3-sulfate, can be isolated prior to the treatment with aqueous sodium carbonate or aqueous sodium hydroxide. Desilation of (10) can be accomplished using a fluoride based reagant such as sodium fluoride, or alternatively, desilylation and cation exchange of compound 9 using an aqueous base, such as sodium hydroxide, affords the sodium-6-hydroxyequilenin-3-sulfate (2).

The 6-hydroxyequilenins of this invention were shown to be estrogens by virtue of their ability to bind to the estrogen receptor. The following summarizes the procedure used and results obtained Evaluation of Binding Affinities to ERα and ERβ

Representative examples of the invention were evaluated for their ability to compete with 17β-estradiol for both ERα and ERβ in a conventional radioligand binding assay. This test procedure provides the methodology for one to determine the relative binding affinities for the ERα or ERβ receptors. The procedure used is briefly described below.

Preparation of receptor extracts for characterization of binding selectivity. The ligand binding domains, conveniently defined here as all sequence downstream of the DNA binding domain, were obtained by PCR using full length cDNA as templates and primers that contained appropriate restriction sites for subcloning while maintaining the appropriate reading frame for expression. These templates contained amino acids $M_{250}$-$V_{595}$ of human ERα [Green, et al., Nature 320: 134-9 (1986)] and $M_{214}$-$Q_{530}$ of human ERβ [Ogawa, et al., Biochemical & Biophysical Research Communications 243: 122-6 (1998)]. Human ERβ was cloned into pET15b (Novagen, Madison Wis.) as a Nco1-BamH1 fragment bearing a C-terminal Flag tag. Human ERα was cloned as for human ERβ except that an N-terminal His tag was added. The sequences of all constructs used were verified by complete sequencing of both strands.

BL21(DE3) cells were used to express the human proteins. Typically a 10 mL overnight culture was used to inoculate a 1 L culture of LB medium containing 100 μg/mL of ampicillin. After incubation overnight at 37° C., IPTG was added to a final concentration of 1 mM and incubation proceeded at 25° C. for 2 hours. Cells were harvested by centrifugation (1500× g), and the pellets washed with and resuspended in 100 mL of 50 mM Tris-Cl (pH 7.4), 150 mM NaCl. Cells were lysed by passing twice through a French press at 12000 psi. The lysate was clarified by centrifugation at 12,000×g for 30 minutes at 4° C. and stored at −70° C.

Evaluation of extracts for specific [$^3$H]-estradiol binding. Dulbecco's phosphate buffered saline (Gibco, 1× final concentration) supplemented with 1 mM EDTA was used as the assay buffer. To optimize the amount of receptor to use in the assay, [$^3$H]-17β-estradiol (New England Nuclear; final concentration=2 nM)±0.6 μM diethylstilbestrol and 100 μL of various dilutions of the E. coli lysate were added to each well of a high binding masked microtiter plate (EG&G Wallac). The final assay volume was 120 μL and the concentration of DMSO was ≦1%. After incubation at room temperature for 5-18 hours, unbound material was aspirated and the plate washed three times with approximately 300 μL of assay buffer. After washing, 135 μL of scintillation cocktail (Optiphase Supermix, EG&G Wallac) was added to the wells, and the plate was sealed and agitated for at least 5 minutes to mix scintillant with residual wash buffer. Bound radioactivity was evaluated by liquid scintillation counting (EG&G Wallac Microbeta Plus).

After determining the dilution of each receptor preparation that provided maximum specific binding, the assay was further optimized by estimating the $IC_{50}$ of unlabelled 17β-estradiol using various dilutions of the receptor preparation. A final working dilution for each receptor preparation was chosen for which the $IC_{50}$ of unlabelled 17β-estradiol was 2-4 nM.

Ligand binding competition test procedure. Test compounds were initially solubilized in DMSO and the final concentration of DMSO in the binding assay was ≦1%. Eight dilutions of each test compound were used as an unlabelled competitor for [$^3$H]-17β-estradiol. Typically, a set of compound dilutions would be tested simultaneously on human ERα and ERβ. The results were plotted as measured DPM vs. concentration of test compound. For dose-response curve fitting, a four parameter logistic model on the transformed, weighted data was fit and the $IC_{50}$ was defined as the concentration of compound decreasing maximum [$^3$H]-estradiol binding by 50%.

Binding affinities for ERα and ERβ (as measured by $IC_{50}$) for representative examples of the invention are shown in Table (1).

TABLE 1

Estrogen receptor binding affinities of compounds of the invention

| Compound | ER-β $IC_{50}$ (nM) | ER-α $IC_{50}$ (nM) |
|---|---|---|
| 1 | 123 | 2183 |
| 5 | 16 | 238 |

The results obtained in the standard pharmacologic test procedure described above demonstrate that the compounds of this invention bind both subtypes of the estrogen receptor. The $IC_{50}$s are generally lower for ERβ, indicating these compounds are preferentially ERβ selective ligands, but are still considered active at ERα. Compounds of this invention will exhibit a range of activity based, at least partially, on their receptor affinity selectivity profiles. Since the compounds of the invention bind ER-β with higher affinity than ER-α, they will be useful in treating or inhibiting diseases that can be modulated via ER-β.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. Effective administration of the compounds of this invention may be given at an oral dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the recipient's bloodstream, including orally, via implants, parentally (including intravenous, intraperitoneal, intraarticularly and subcutaneous injections), rectally, intranasally, topically, ocularly (via eye drops), vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The preparation of representative examples of this invention is described below. While the present invention has been described with specificity in accordance with certain of its preferred embodiments, the following examples serve only to illustrate the invention and are not intended to limit the same.

EXAMPLE A

6-Hydroxy-3,17β-diacetoxydihydroequilenin (4)

Ref: M.Harnik, *Israel Journal of Chemistry*, Vol.3, 1965, p. 183-192.

A mixture of 6-keto-7-bromo-17β-estradiol-diacetate (3, 3.0 g, 0.007 mol) and $CaCO_3$ (3.3 g, 0.033 mol) in dimethylacetamide (50 mL) was refluxed for 2 h. TLC (EtOAC-hexanes 4:6) showed no starting material, mostly the desired product. The reaction mixture was cooled to 25° C., concentrated in vacuum to dryness, and the residue treated with EtOAc (150 mL) and 0.1 N HCl (75 mL). The aqueous layer was extracted with EtOAc (50 mL), and combined organic layer and extracts were washed with water, saturated $NaHCO_3$, and brine, dried over $Na_2SO_4$, and concentrated in vacuum to dryness to give 4 (1.5 g, 62.5%) as a light brown oil.

$^1$H NMR ($CDCl_3$): 7.91 (d, 1H, J=10.2 Hz); 7.86 (d, 1H, J=2.7 Hz); 7.26 (dd, 1H, J=2.8, 10.1 Hz); 6.56 (s, 1H); 5.07 (m, 1H); 4.88 (m, 1H, 17□-H); 3.25-3.08 (m, 2H); 2.87 (m, 1H); 2.46-1.73 (m, 6H); 2.36 (s, 3H, —OAc); 2.10 (s, 3H; —OAc); 0.73 (s, 3H, —$CH_3$).

GC/MS: MW 368.

EXAMPLE B

6-Hydroxy-3,17β-dihydroequilenin (5)

To a solution of 4 (5.0 g, 0.014 mol) in methanol (50 mL), $K_2CO_3$ (3.75 g, 0.027 mol) was added at 25° C., and the slurry was stirred for 18 h. Reaction mixture turned dark pink. TLC (EtOAC-hexanes 4:6) showed no starting material, mostly the desired product. The reaction mixture was concentrated in vacuum to dryness, and the residue was chromatographed on Silica Gel column using gradient eluation (hexanes-EtOAc, 100:0 to 50:50) to give 5 (3.3 g, 85.5%) as a colorless oil.

$^1$H NMR (DMSO): 9.48 (s, 1H; —OH); 9.41 (s, 1H; —OH); 7.69 (d, 1H, J=10.1 Hz); 7.34 (d, 1H, J=2.6 Hz); 7.02 (dd, 1H, J=2.8, 10.00 Hz); 6.48 (s, 1H); 4.64 (d, 1H, J=5.3 Hz; 17β-OH); 3.71 (m, 1H; 17□-H); 3.09-1.54 (m, 9H); 0.55 (s, 3H, —$CH_3$).

GC/MS: MW 282.

EXAMPLE C

6-Hydroxyequilenin (1)

Ref: Shwarz S., et al, *Tetrahedron,* 50(36), 10709-10720 (1994)

To a solution of 5 (2.5 g, 0.009 mol) in triethylamine (11 mL, 0.080 mol) and DMSO (20 mL), sulfur trioxide trimethylamine complex (5.6 g, 0.040 mol) was added at room temperature with stirring. The mixture was stirred for 3 h at 25° C., then diluted with water (150 mL), and extracted with EtOAc (3×50 mL). The combined organic extracts were washed with 0.1 N HCl and water, dried over $Na_2SO_4$, and concentrated in vacuum to dryness to afford 1 (2.3 g) as oily solid. The crude product was recrystallized from iPrOH-toluene to give 1 (1.3 g, 51.5%) as a white solid.

$^1$H NMR (DMSO): 9.65 (s, 1H, —OH); 9.50 (s, 1H; —OH); 7.71 (d, 1H, J=10.1 Hz); 7.40 (d, 1H, J=2.8 Hz); 7.05 (dd, 1H, J=28.6, 10.1 Hz); 6.62 (s, 1H); 3.08-1.71 (m, 9H); 0.69 (s, 1H; —$CH_3$).

GC/MS: MW 426.

EXAMPLE D

6-O-t-butyldimethylsilyl Equilenin-3,17β-diacetate (6)

Method A

A mixture of 6-hydroxyequilenin-3,17β-diacetate (4, 5.0 g, 13.58 mmol), tert. butyldimethylsilyl chloride (3.07 g, 20 mmol) and imidazole (2.78 g, 40 mmol) in dimethylformamide (40 ml) was stirred at ambient temperature under $N_2$ atmosphere. After 1 hour, the reaction mixture was poured onto an ice-cold saturated sodium bicarbonate solution (200 ml). It was extracted with ethyl acetate (40 ml×3). The combined ethyl acetate extracts were washed with water (100 ml) and brine (100 ml), dried ($Na_2SO_4$) and evaporated to give 6.2 g of the crude product. The crude product was purified by column chromatography (hexane:ethyl acetate 8.5:1.5). Upon evaporation of the appropriate fractions, product 6 (4.96 g, 76%) was obtained as a white solid.

$^1$ H-NMR (300 MHz, CDCl3): δ 7.90 (d, J=9.1 Hz, 1H), 7.83 (d, J=2.5 Hz, 1H), 7.23 (dd, J=9.1, 2.5, 1H), 6.62 (s, 1H), 4.88 (dd, J=9.1, 6.9, 1H), 3.0-3.3 (m, 2H), 2.88 (m, 1H), 2.44 (m, 1H), 2.36 (s, 3H), 2.17 (m, 2H), 2.1 (s, 3H), 1.7-1.89 (m, 3H), 1.07 (s, 9H), 0.74 (s, 3H), 0.29 (s, 3H), 0.26 (s, 3H).

GC-MS: 482.

HPLC (purity area %): 99.34%.

Method B

A 3-necked 1000-mL Morton flask equipped with a thermocouple/controller, overhead stirrer and nitrogen inlet was charged 40.3 g (0.0896 mole) of the bromoketone 3, 44.89 g (0.448 mole), anhydrous calcium carbonate, and 400 mL of dimethylacetamide (DMAC). The mixture was heated at 100° C. under nitrogen for 10 hr. HPLC analysis of an aliquot of the reaction mixture indicated 2.4% (area % at 255 nm) of the starting bromoketone was left in the mixture. The slurry was cooled to 20 to 25° C. and filtered. The solids on the filter were washed once with 50 mL DMAC and once with 25 mL DMAC. HCl (300 mL of 1M) and ice was added to the combined filtrates. The slurry was diluted to a total volume of 1500 mL by the addition of water. After vigorous stirring the solid was separated by filtration (3 to 20° C.). The solid on the filter was washed with 50 mL of 1M HCl and three times using 100 mL of water for each wash. Drying the solid for 5 days at 40° C. afforded 33.9 g of crude 4 (90% area by HPLC). FTIR spectrum of the product showed strong acetate carbonyl absorptions at 1731 and 1766 $cm^{-1}$ with none of the ketone carbonyl observed at 1687 $cm^{-1}$.

The crude diacetate 3 was converted to the TBDMS derivative without further purification. The diacetate 4 (33.8 g, 0.0920 mole) was charged into a 500 mL Ehrlenmeyer flask along with 200 mL of DMF. While stirring magnetically under $N_2$, 11.7 g (0.166 mole) of imidazole and 24.2 g (0.161 mole) of t-butyldimethylsilyl chloride were added. The resulting solution was stirred at 20 to 25° C. for 18 hr and then poured onto a mixture of 200 mL of 1M HCl and ca. 400 mL of ice. After allowing the ice to melt, the mixture was extracted once with 500 mL of ethyl acetate and twice with 250 mL of ethyl acetate. The combined extracts were washed with 500 mL of water followed by 500 mL of 10% brine solution. After the organic phase drying over magnesium chloride and removing the solvent by evaporation under reduced pressure (25-35 mm, 50° C.), 35.1 g of crude 4 was recovered. The silyl ether was purified by chromatography on 50 g of silica (Baker 40 μm flash chromatography grade), eluting with mixtures of dichloromethane and hexane. The elution fractions were analyzed by HPLC and those containing the silyl ether were combined. Evaporation of the solvents under reduced pressure (25-35 mm, 50° C.), afforded 24.9 g (56% yield) of the silyl ether diacetate 6, a yellow solid. LC/MS data was consistent with the expected structure.

EXAMPLE E

6-O-t-butyldimethylsilyl equilenin-17β-ol (7)

Method A

To a solution of the diacetate 6 (0.35 g, 0.72 mmol) in methanol (5 ml) was added anhydrous potassium carbonate (0.1 g, 0.72 mmol). The reaction mixture was stirred at ambient temperature for 22 h. The reaction mixture was evaporated. To the residue, water (25 ml) was added and neutralized with 1M HCl. The aqueous layer was extracted with ethyl acetate (20 ml×3), washed with water (30 ml), brine (30 ml), dried and evaporated to give 0.29 g of the crude product 7. Silica gel column chromatography of the crude product (hexane:ethyl acetate 7.5:2.5) gave pure white solid product 7 (0.194 g, 68%).

$^1$H-NMR (300 MHz, CDCl3): δ 7.80 (d, J=9.1 Hz), 7.48 (d, J=2.7 Hz), 7.11 (dd, J=9.1, 2.7, 1H), 6.56 (s, 1H), 5.75 (brs, 1H), 3.96 (m, 1H), 3.04-3.26 (m, 2H), 2.78 (m, 1H), 2.37 (m, 1H), 2.08-2.26 (m, 2H), 1.6-1.82 (m, 4H), 1.07 (s, 9H), 0.71 (s, 3H), 0.29 (s, 3H), 0.26 (s, 3H).

HPLC (purity area %): 99.8%.

Method B

The diacetate 6 (3.17 g, 6.57 mmole) was charged into a 50 mL 3-necked round bottomed flask fitted with a magnetic stirrer, thermocouple, and an $N_2$ inlet. THF (16 mL) and 10 mL of MeOH were added followed by the dropwise addition of 9.9 mL of 1 M solution of LiOMe in MeOH. The mixture was refluxed for 3.5 hr and allowed to cool to 20 to 25° C. LC/MS analysis of the reaction mixture indicated 71% diol and 2% 17-monoacetate (area % at 220 nm). Concentrated HCl (0.9 mL) was added to the reaction mixture and the solvents were removed on a rotary evaporator (25-35 mm, 50° C.). The residue from the evaporation was dissolved in 50 mL of ethyl acetate and washed three time using 50 mL of distilled water for each wash. The ethyl acetate solution was dried over $MgSO_4$, filtered and evaporated on a rotary evaporator (25-35 mm, 50° C.) affording 1.42 g of the crude diol 7, a rust-brown solid, yield 52.2%. The FTIR spectrum (KBr) showed a strong OH band at 3390, aromatic at 1600, substituted naphthalene at 851/838 and a silyl ether band at 1062 cm$^{-1}$. LC/MS confirmed the molecular weight as 398. This crude was used without purification in the following reaction.

EXAMPLE F

6-O-t-butyldimethylsilyl Equilenin (8)

To a solution of the diol 7 (1.3 g, 3.26 mmol) in dimethyl sulfoxide (10 ml) at ambient temperature was added Et3N (0.99 g, 9.78 mmol) and Et$_3$N—SO$_3$ (1.47 g, 8.1 mmol). After 30 min, the pink reaction mixture was poured into water (100 ml), stirred for 5 min. The aqueous solution was extracted with ethyl acetate (24 ml×4), washed with water (25 ml×2), brine (50 ml×2), dried and evaporated to give purple colored solid crude product. Silica gel column chromatography (hexane:ethyl acetate 21:4) of the crude product gave light pink colored solid product 8 (0.88 g, 68%).

$^1$H-NMR (300 MHz, DMSO-d$_6$): δ 9.64 (s, 1h), 7.74 (d, J=9.1 Hz, 1H), 7.34 (d, J=2.5 Hz, 1H), 7.06 (dd, J=9.1, 2.5 Hz), 6.59 (s, 1H), 2.94-3.19 (m, 3H), 2.61 (m, 1H), 2.23-2.46 (m, 2H), 1.98 (m, 1H), 1.68-1.91 (m, 2H), 1.04 (s, 9H), 0.67 (s, 3H), 0.26 (s, 3H), 0.23 (s, 3H).

GC-MS: 99.6%

HPLC (purity area %): 97.7%.

EXAMPLE G

Triethylammonium-6-O-tbutyldimethylsilyl-equilenin-3-sulfate with TRIS (9)

To a solution of 8 (0.81g, 2.04 mmol) in anhydrous THF (50 ml) was added triethylamine sulfur trioxide complex (0.64 g, 3.48 mmol) at 22° C. Stirred for 20 h at 22° C., then the reaction mixture was evaporated. To the residue, a solution of tris(hydroxymethyl)aminomethane (TRIS, 0.55 g) in water (150 ml) was added. The hazy solution was extracted with diethyl ether (100 ml×3). The aqueous layer (200 ml) was concentrated (180 ml) on a rotovap and the resulting solution was lyophilized to give 9 stablized with TRIS, as a tan colored solid (1.65 g, 76%).

$^1$H-NMR (300 MHz, DMSO-d$_6$): δ 7.83 (m, 2H), 7.38 (dd, J=9.1, 2.4 Hz), 6.65 (s, 1H), 3.01-3.26 (m, 3H), 2.75 (q, J=7.2 Hz, 6H), 2.61 (m, 1H), 2.23-2.47 (m, 2H), 1.90 (m, 1H), 1.71-1.94 (m, 2H), 1.03 (m, 18H), 0.65 (s, 3H), 0.23 (s, 3H), 0.21 (s, 3H).

HPLC (purity area %): 95.7%.

EXAMPLE H

Sodium-6-hydroxyequilenin-3-sulfate (2)

Method A
Step A
Sodium-6-0-t-butyldimethylsilyl Equilenin-3-Sulfate (10)

Anhydrous THF (40 mL) was delivered by cannula into a 100-mL 3-necked round bottomed flask containing TBDMS protected 6-hydroxyequilenin 8 (0.888 g, 2.24 mmole). The triethylamine sulfur trioxide complex (0.822 g, 0.049 mole) was then added under a nitrogen atmosphere. The reaction mixture was stirred for 2¼ hr at 20 to 25° C. Analysis by LC/MS indicated 98.6% of the expected sulfate and 1.4% unreacted 8. The THF was evaporated under reduced pressure (25 to 35 mm Hg) at 35° C. Distilled water (35 mL) was added along with sodium carbonate (0.88 g, 8.3 mmole). The gummy aqueous mixture was extracted with 15 mL of ethyl acetate. The aqueous phase containing the sulfate 10 was sampled and analyzed by LC/MS. The mass spectrum (positive mode) of the major peak showed three fragments: M/Z 477, M+1; 397, M-SO$_3$; 398, M-SO$_3$+1; and 419, M-SO$_3$+Na. A similar fragmentation pattern was observed in the negative mode. UV scans across the major peak were identical indicating the peak was homogeneous. The aqueous solution of 10 was used in the following step without further purification.

Step B
Sodium-6-Hydroxyequilenin-3-Sulfate (2)

MeOH (100 mL) was added to the aqueous mixture of the sulfate ester (see above). Anhydrous sodium fluoride (0.206 g) was added to the reaction mixture. After 4.5 hr stirring at 25° C., LC/MS analysis indicated 53% of the de-silylated sulfate ester 2 and 36% unreacted 10. After stirring for a total of 18 hr at 20 to 25° C., analysis by LC/MS 85% of the de-silylated sulfate 2, 4.8% of the starting material 10 and 0.7% of the 3-hydroxy-6-TBDMS 8. The MeOH was removed by evaporation under reduced pressure (25 to 35 mm Hg, 40° C.). Distilled water (100 mL) was added to the residue and the aqueous solution was extracted with diethyl ether (3×100 mL). Analysis of the aqueous phase by LC/MS indicated 90.1% of the 6-hydroxy-3-sulfate 2 (ret. time 3.30 min) and two minor impurities: 3.88 min (1.4%) and 4.40 min (4.9%). The crude material was dissolved in anhydrous ethanol (50 mL) and filtered to remove a small amount of insolubles. LC/MS analysis of the filtrate indicated the 94.4% of 2 and 2.0% and 3.2% of the other impurities (ret. times 3.6 and 4.0 min respectively). Evaporation of the solvent (25 to 35 mm Hg, 40° C.) afforded 0.672 g of 2 (78% yield based on the sulfated TBDMS ether 7). FTIR (KBr) of the product was consistent with the expected structure 2 with strong bands at 1726, 1640, 1413, 1260, 1054, 800 and 644 cm$^{-1}$. The product 2 was combined with 0.448 g of tris(hydroxymethyl) aminomethane (TRIS, as stabilizer) in 100 mL of distilled water and lyophilized to a fluffy tan powder (1.107 g).

$^1$H-NMR (300 MHz, DMSO-d$_6$): δ 9.82 (s, 1H), 7.89 (d, J=2.0 Hz, 1H), 7.77 (d, J=7.0 Hz, 1H), 7.33 (dd, J=7.0, 2.0 Hz), 6.69 (s, 1H), 3.0-3.2 (m, 3H), 2.65 (m, 1H), 2.27-2.43 (m, 2H), 1.87-2.1 (m, 2H), 1.73-1.83 (m, 1H), 0.70 (s, 3H).

FTIR (KBr): 1726, 1640, 1413, 1260, 1054, 800 and 644 cm$^{-1}$.

LC/MS: 95%.

Method B

To 9 (0.03 g, 0.05 mmol) a solution of aqueous sodium hydroxide solution (4.5 mg in 2.0 ml of water) was added and stirred at ambient temperature. After 2 h, water (10 ml) was added and the solution was extracted with diethyl ether (10 ml×2). The aqueous portion was lyophilized to give 0.025 g (86% yield) of 2 as a light ash colored solid.

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound which is 6-O-t-butyldimethylsilyl equilenin-3,17β-diacetate.

2. A compound which is 6-O-t-butyldimethylsilyl equilenin-17β-ol.

3. A compound which is 6-O-t-butyldimethylsilyl equilenin.

4. A composition comprising triethylammonium-6-O-t-butyldimethylsilyl-equilenin-3-sulfate and tris(hydroxymethyl)aminomethane.

5. A compound which is sodium-6-O-t-butyldimethylsilyl equilenin-3-sulfate.

* * * * *

UNITED STATES PATENT AND TRADEMARK OFFICE
CERTIFICATE OF CORRECTION

PATENT NO. : 7,601,857 B2  Page 1 of 1
APPLICATION NO. : 11/209066
DATED : October 13, 2009
INVENTOR(S) : Megati et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 993 days.

Signed and Sealed this

Fifth Day of October, 2010

David J. Kappos
*Director of the United States Patent and Trademark Office*